US006684918B1

(12) United States Patent
Thilly et al.

(10) Patent No.: US 6,684,918 B1
(45) Date of Patent: Feb. 3, 2004

(54) TEAT NOZZLE FOR DOSING DEVICE WITH CONNECTION MEANS

(75) Inventors: Jacques Thilly, Rixensart (BE); Christian Vandecasserie, Rixensart (BE)

(73) Assignee: SmithKline Beecham Biologicals s.a., Rixensart (BE)

( * ) Notice: Subject to any disclaimer, the term of this patent is extended or adjusted under 35 U.S.C. 154(b) by 0 days.

(21) Appl. No.: 09/937,040

(22) PCT Filed: Mar. 17, 2000

(86) PCT No.: PCT/EP00/02393

§ 371 (c)(1),
(2), (4) Date: Dec. 13, 2001

(87) PCT Pub. No.: WO00/57835

PCT Pub. Date: Oct. 5, 2000

(30) Foreign Application Priority Data

Mar. 27, 1999 (GB) ............................................ 9907014

(51) Int. Cl.$^7$ ................................................ A61B 19/00

(52) U.S. Cl. .......................... 141/25; 141/27; 141/330; 141/384; 604/414

(58) Field of Search ........................... 141/25, 27, 329, 141/330, 383, 384; 604/240, 241, 411, 414, 415, 905

(56) References Cited

U.S. PATENT DOCUMENTS

| | | | | |
|---|---|---|---|---|
| 3,489,147 A | | 1/1970 | Shaw | |
| 4,127,126 A | | 11/1978 | Schunk | |
| 4,784,641 A | | 11/1988 | White | |
| 5,697,918 A | | 12/1997 | Fischer et al. | |
| 5,772,652 A | * | 6/1998 | Zielinski | 604/411 |
| 5,891,129 A | * | 4/1999 | Daubert et al. | 604/411 |

FOREIGN PATENT DOCUMENTS

| | | |
|---|---|---|
| DE | 1 263 991 | 3/1968 |
| DE | 315033 | 7/1983 |
| EP | 0 499 481 | 8/1992 |
| FR | 2 256 752 | 8/1975 |
| FR | 2 427 960 | 1/1980 |

OTHER PUBLICATIONS

Translation of DE 3152033.*

* cited by examiner

*Primary Examiner*—Gene Mancene
*Assistant Examiner*—Peter deVore
(74) *Attorney, Agent, or Firm*—Edward R. Gimmi; Charles M. Kinzig

(57) ABSTRACT

A teat nozzle suitable for pediatric oral dosing of a fluid medicament comprising a tubular conduit which is engageable with a socket, and has at least one engagement part which can engage with an internal thread in the socket. The teat nozzle facilitates connection between the conduit and the socket. Dosing devices such as syringes and squeezable capsules provided with the nozzle, and a connection means for a vial having such a socket, are also described.

13 Claims, 5 Drawing Sheets

TEAT NOZZLE FOR DOSING DEVICE WITH CONNECTION MEANS

This invention relates to a novel device being a nozzle suitable for the oral administration of a paediatric fluid medicament from a dosing device such as a dosing syringe or a collapsible capsule. In particular the invention relates to such a nozzle which facilitates connection between containers of the fluid medicament. The invention also relates to a dosing device provided with such a nozzle, and to a connector device suitable for enabling a dosing device such as a syringe or compressible capsule having such a nozzle to be connected to a container such as a pharmaceutical vial.

Devices for the oral administration of fluid medicaments to paediatric patients are known, generally comprising a container for the medicament, in particular a dosing syringe provided with a teat nozzle in the form of a conduit for the medicament, terminating in a nozzle opening. Another such device comprises a compressible capsule, containing the liquid medicament, made of soft plastic material also provided with a teat nozzle in the form of a conduit for the medicament, terminating in a nozzle opening. Such devices are particularly suitable for use with very young children and babies who are incapable of drinking a fluid medicament from a cup or spoon, and can only suck from a teat. In use the nozzle is inserted into the mouth of a paediatric patient and a liquid medicament from the syringe is injected into the patient's mouth. One such fluid medicament is that provide for treatment (curative and/or prophylactic) of the Rotavirus infection in paediatric patients.

It is known to provide syringes and like devices with connection means so that they can be connected to a second container of the medicament, in particular a vial of the medicament, e.g. by a screw connection. Such vials are often provided closed by a closure which includes a puncturable rubber seal, and connection means for such vials are known which include a hollow puncturing spike which can be driven through the seal, and through the hollow interior of which the medicament can be extracted from the vial into for example a dosing syringe.

Such connection means are required to comply with an international standard, ISO 594/1 "Conical fittings with a 6% (Luer) taper for syringes, needles and certain other medical equipment", which specifies their mode of construction, shape and dimensions, so as to enable interconnectability of such connection means.

A problem exists with dosing syringe nozzles made according to this international standard in providing connection means which can be readily adapted for use with oral dosing of small children and babies. It is an objection of this invention to provide a connection means which in part at least solves this problem.

According to the present invention a teat nozzle suitable for paediatric oral dosing of a fluid medicament comprises a tubular conduit having an internal channel along which a fluid medicament may be caused to flow toward a nozzle opening of the conduit, characterised in that the conduit is engageable in a male-female co-operation with a female socket, and the conduit is provided externally with at least one engagement part which can engage with an internal thread in such a female socket, to thereby facilitate connection between the conduit and the socket.

The conduit is suitably externally in the form of a substantially cylindrical tube having at least its part immediately adjacent to and upstream of the nozzle opening tapering in a shallow cone being narrowest at the nozzle opening end of the cone. The base of such a cone is adjacent to the cylindrical part of the conduit upstream of the cone, and the cross section of the base of the cone may be the same or different, e.g. smaller to the cross section of an immediately adjacent cylindrical part. Such a cone may for example comprise 25–75% of the length of the teat nozzle extending upstream from the nozzle opening. Alternatively all or substantially all of the conduit may be externally of a shallow conical shape. Alternatively the conduit may have a cylindrical part immediately adjacent to and extending upstream of the nozzle opening, and of a shallow conical shape over its further upstream part, the cylindrical part meeting the apex of the cone.

The term "cylindrical" as used herein includes oval and other distorted circular cross sections. The term "conical" as used herein includes truncated cones, and includes both true cones, i.e. with straight sides and circular cross sections at all points along their base-apex axis, and distorted cones, e.g. with stepped or concave or convex curved sides and oval and other distorted circular cross sections. A typical amount of conical taper is ca. 2–10°. For example the cone may be of the 6% cone shape defined in ISO 594/1 "Conical fittings with a 6% (Luer) taper". The terms "upstream" and "downstream" as used herein refer to the direction in which the fluid medicament flows from a dosing device through the nozzle towards the patient's mouth during dosing to a patient.

Such a shallow cone shape is particularly advantageous for use as a teat which can be inserted, for dosing, into the mouth of a small child or baby, and which will be comfortable for such a patient.

The conduit may be shaped and dimensioned externally out of compliance with ISO 594/1 mentioned above, in particular being made larger than the dimensions given therein, so that it is impossible to fit a standard hypodermic needle to the conduit. This would prevent any accidental use of the nozzle of the invention with such a needle when it is intended for oral use. This is important because dosing devices such as syringes etc. intended for oral use are not necessarily provided for use in a sterile state, whereas for use with a hypodermic needle for injections through the skin a sterile dosing device must be used.

When the conduit comprises a conical part and an upstream cylindrical part, the engagement part(s) is/are preferably provided upstream of the conical part, for example immediately adjacent upstream of the conical part, or at the junction between the conical part and the cylindrical part. For example the engagement part(s) may be provided at or immediately upstream of the wide base of such a conical part. When the conduit comprises a cylindrical part and an upstream conical part, the engagement part(s) is/are preferably provided upstream of the cylindrical part, for example immediately adjacent upstream of the cylindrical part, or at the junction between the conical part and the cylindrical part. For example the engagement part(s) may be provided at or immediately upstream of the wide base of such a conical part. When substantially the whole of the conduit is externally conical the engagement part(s) may be provided at any point upstream of the nozzle opening. Preferably the engagement part(s) may be provided between 25–75% of the length between the nozzle opening and the other end of the teat nozzle, e.g. the point where the nozzle is joined to a dosing device.

The at least one engagement part(s) may be suitable for engagement with a helical or part helical internal thread on the said female socket. A screw thread enables a tight connection to be made, which can help resist build up of pressure within the device and socket. Preferably the engagement parts comprise at least two, but suitably two, rounded bumps, e.g. wings, on the outer surface of the conduit. Such bumps may for example be smoothly curved e.g. substantially hemispherical or rounded conical, and may be regularly circumferentially disposed around the conduit. For example if two such bumps are present they may be oppositely disposed around the circumference, e.g. 180° apart. Such bumps may be engageable with an internal helical thread on the female socket having a section corresponding to that of the bumps. The use of such bumps is advantageous as they can have a smoothly rounded profile which is comfortable to the mouth of small children and babies for which the device is used for oral dosing.

In another aspect the invention also provides a dosing device suitable for dosing a liquid medicament, particularly such a device suitable for oral dosing, and being provided with a teat nozzle as described above. Such a dosing device is preferably a syringe, e.g. a tubular barrel provided with a piston which can be driven toward a nozzle opening of the syringe to dispense fluid contents of the barrel, e.g. a single dose of medicament, through the nozzle, or a collapsible capsule, e.g. a envelope made of a flexible soft plastics material, e.g. containing a single dose of medicament, which can be compressed to reduce its internal volume and to drive the fluid contents out through a nozzle part of the capsule. The term "dosing device" as used herein is not intended to limit the invention to dosing devices in which the dose administered is measured and/or controlled by a meter, although the invention may be used with metered dosing devices.

Preferably the teat nozzle of the invention may be made integrally with a dosing device which includes a reservoir for a liquid medicament, for example the teat nozzle may comprise the integral nozzle part of a dosing syringe or collapsible capsule. The present invention therefore further provides a dosing device having a teat nozzle as described above as its integral nozzle. Such an integral syringe and teat nozzle may be made of conventional materials such as glass or preferably of plastic. Such an integral collapsible capsule and nozzle may be made of conventional materials such as soft plastic.

Alternatively the teat nozzle of the invention may be made as a separate part attachable to a dosing device which includes a reservoir for a liquid medicament, such as a dosing syringe or a collapsible capsule, and for this purpose the conduit may be provided at its upstream end with a suitable connection for a dosing device, e.g. of a syringe or of a collapsible capsule. For example the connection may comprise a widening of the internal channel to enable connection with a male nozzle part of the dosing device. The present invention therefore further provides a teat nozzle being a separate part attachable to a dosing device, for example having a conduit provided at its upstream end with a connection to enable connection with a dosing device such as a syringe or collapsible capsule. If provided as such a separate part extreme care must be taken to ensure that the separate part cannot become detached from the dosing device during use in oral dosing, with the consequent risk of swallowing of the part by the patient.

The teat nozzle of the invention may be provided with a protective removeable closure, e.g. a flexible conforming cap, to prevent contamination etc., which is removed before use.

By means of the engagement of the conduit with the female socket the conduit is made connectable with the socket and consequently a fluid medicament may flow between the conduit and the socket. If the conduit and socket are themselves in communication with respective containers such as the reservoir of a dosing device and a vial, the fluid medicament may be transferred therethrough from one container to the other. For example a vial may contain a medicament provided for reconstitution, and a syringe or collapsible capsule may contain a medium for reconstitution, and the medium may be transferred from the syringe or capsule into the vial via the connection to reconstitute the medicament, and the reconstituted medicament may then be transferred back into the syringe or capsule for dosing to the patient. Alternatively the vial may be provided containing a liquid medicament which may be transferred from the vial to the dosing device.

In another aspect of this invention there is provided a connection means by which the teat nozzle of the invention may be connected to a container of the medicament.

A preferred form of such a connection means is provided for a container which is closed with a puncturable seal, the connection means having a female socket having an internal thread which is engageable with the engagement parts of the teat nozzle such that the nozzle may make a fluid connection with the socket, a hollow puncturing spike having an internal channel therein which is in communication with the socket, the puncturing spike able to be driven through the puncturable seal of the container to thereby establish fluid communication between the contents of the container and the teat nozzle.

The container may for example comprise a pharmaceutical vial, and may for example be provided containing a dried solid medicament for reconstitution with reconstitution fluid, e.g. an aqueous medium, passed into the vial via the teat nozzle, socket and spike, and subsequently withdrawn along the same route into for example a dosing device such as a dosing syringe or a collapsible capsule.

The female socket preferably corresponds internally closely in shape and dimensions to the external shape of at least part of the teat nozzle of the first aspect of the invention.

The connection means may comprise various constructions, and some suitable constructions are discussed below.

One suitable construction of the connection means comprises a substantially bell-shaped structure of internal size, shape and dimensions enabling it to fit closely over the closure, including a puncturable seal, of a pharmaceutical vial, and the bell being optionally provided with clip means to enable the bell-shaped structure to be retained upon the vial closure, the hollow puncturing spike extending downwardly internally within the bell, preferably co-axially with the longitudinal axis of the cylindrical bell, a female internally threaded socket being provided externally on the base of the bell and in communication with the hollow channel of the puncturing spike.

Another suitable construction of the connection means comprises a tubular body which can be attached to the vial (e.g. by known means) and which when in place on the vial extends upwardly from the mouth of the vial to define internally a tubular chamber having the puncturable seal at a lower end, a piston, provided in an first upper position relatively more distanced from the seal and being moveable within the tubular body to a second lower position relatively less distanced from the seal, the piston having a connection port comprising the female socket, and a tubular puncture member extending downwardly from the piston, the puncture member having a cannula therethrough communicating with the connection port, movement of the piston from its first position to its second position causing the puncture member to puncture the seal so that in the second position the connection port and the interior of the vial are in communication with each other via the cannula.

In this embodiment the piston may be initially provided mounted on and extending at least partially inside the tubular sleeve (preferably with its puncturing spike within the sleeve). The piston may be mounted in the tubular body by means of a link which may be easily broken, for example by a downward force on the piston. The piston and the tubular body in such a construction may include co-operating guides which encourage the piston to move in a downward direction, i.e. toward the vial seal, and which may prevent relative rotation of the piston and the tubular body. The piston and the tubular body may also include co-operating locking means such that the piston may be locked in place in the tubular body at the lowest end of its downward movement.

Connection means of the general type described above, but without the above-mentioned internally threaded female socket, are known for example being disclosed in EP 0351643A, EP 0587347, EP 0126718A, U.S. Pat. No. 4,564,054, GB 1452418, U.S. Pat. No. 3,977,555 and U.S. Pat. No. 5,350,372.

In use such a connection means may be provided attached to the vial by known means, positioned relative to a pharmaceutical vial provided with a puncturable seal such that the puncturing spike is above and aimed at the seal. The piston may then be moved downwardly toward the vial such that the puncturing spike punctures the seal and thereby provides communication between the interior of the vial and the female socket. The teat nozzle may then be inserted into the female socket and its engagement part(s) engaged with the internal thread of the socket to thereby provide communication between the channel and the interior of the vial, and between the latter and a container in communication with the teat nozzle, e.g. a dosing syringe or collapsible capsule.

Alternatively a teat nozzle comprising part of a dosing device such as a syringe or a collapsible capsule may be engaged with the female socket and force may be applied to the dosing device to move the piston downwards analogously to the above-described manner. This mode of use has the advantage that contact between the user's fingers and the socket is minimised In one mode of use a dosing device such as a syringe or collapsible capsule may contain a reconstitution liquid and the vial may contain a solid, e.g. lyophilised, medicament for reconstitution. When the communication between the dosing device and the interior of the vial has been established as described above the reconstitution liquid may be transferred through the teat nozzle, socket and spike into the vial, and the medicament reconstituted in the vial. The reconstituted medicament, e.g. as a solution, may then be withdrawn into the dosing device.

All of the above-mentioned parts of the device and connection means of the invention may be made of plastics materials by a process of injection or blow moulding. Such plastics materials should be acceptable for contact with pharmaceutical substances, particularly liquid medicaments. In a further aspect the invention therefore provides a mould suitable for the manufacture therein of a device or connection means as described above.

The teat nozzle and/or dosing devices described above, and the connecting means of the invention may be provided together as a kit comprising one or more such teat nozzles and/or dosing devices and one or more connection means. Such a kit comprises a further aspect of this invention. The connection means described above may also be provided attached to a vial, and the combination of the connector and a vial are a further aspect of this invention.

The invention will now be described by way of example only with reference to the accompanying drawings.

Figure 1:
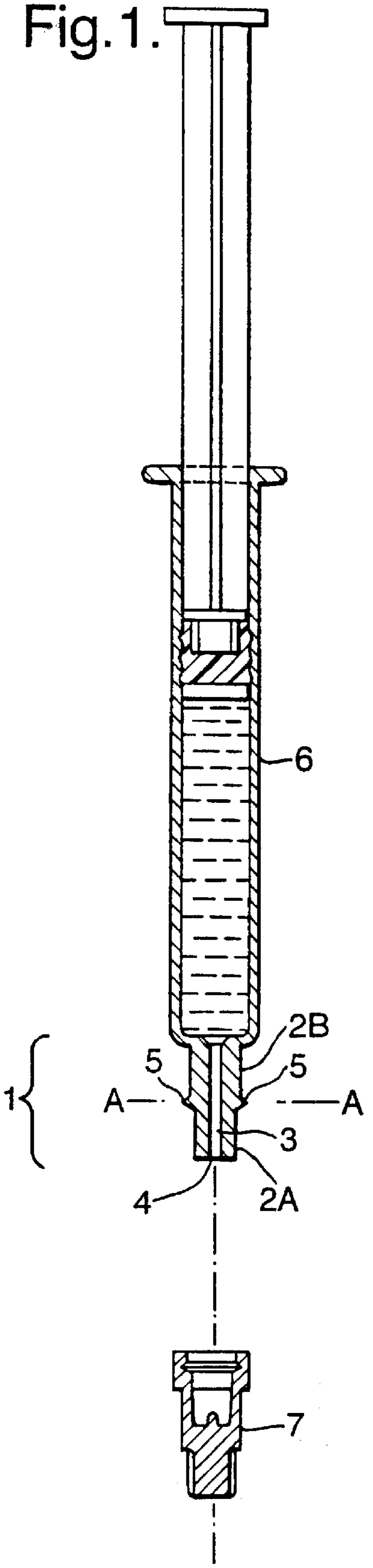
FIG. 1 shows a longitudinal sectional view through a device of the invention formed integrally as part of a dosing device being a syringe.
Figure 2:
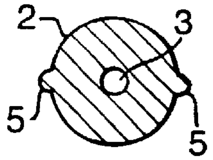
FIG. 2 shows a cross section through the nozzle of the syringe of FIG. 1 about the line A—A.

Referring to FIGS. 1 and 2, a teat nozzle suitable for paediatric oral dosing of a fluid medicament is shown 1 overall. The teat nozzle 1 comprises a tubular conduit 2 having an internal channel 3 along which a fluid medicament may be caused to flow toward a nozzle opening 4 of the conduit, i.e. the "downstream" direction. The conduit 2 is provided externally with two engagement parts 5 in the form of two rounded bumps on the outer surface of the conduit disposed 180° apart around the circumference of the conduit 2, these bumps being substantially hemispherical. The teat nozzle 1 is made as an integral nozzle of a dosing syringe 6, and the conduit 2 and syringe 6 are both made of plastic.

The conduit 2 is in the form of a substantially cylindrical tube having its part 2A, immediately adjacent to and upstream of the nozzle opening 4 in the shape of a tapering shallow cone, of ca. 5° taper angle, being narrowest at the nozzle opening 4 end of the cone. The part 2B of the conduit upstream 2 of the engagement parts 5 is cylindrical, and the cross section of the base of the cone is slightly less than the cross section of the cylindrical part 2B. The bumps 5 are located at the junction of the parts 2A and 2B, i.e. about midway between the nozzle 4 opening end, distal from the syringe 6 and the end of the conduit 2 proximal to syringe 6 which meets the syringe.

Also shown in FIG. 1 is a protective cover 7 which may be fitted onto the teat nozzle 1 to protect and close it. The cover 7 is made of soft rubber to resiliently fit over the teat nozzle 1.

Figure 3B:
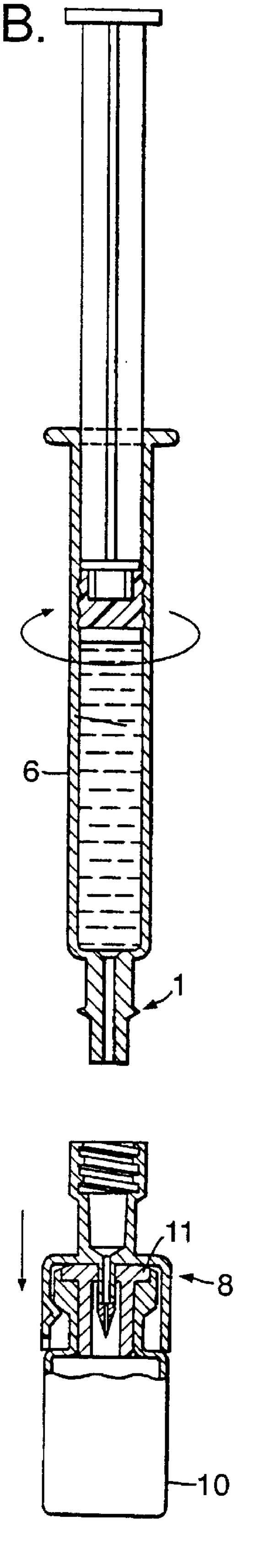
FIG. 3 shows a longitudinal sectional view through a connection means suitable for use with the device of FIGS. 1 and 2, in use.

Referring to FIG. 3 and 4 connection means 8, 9 are shown by which the nozzle 1 of the invention may be connected to a vial 10 of the medicament, the mouth of the vial 10 being closed with a puncturable rubber seal 11 of known type.

Figure 3C:
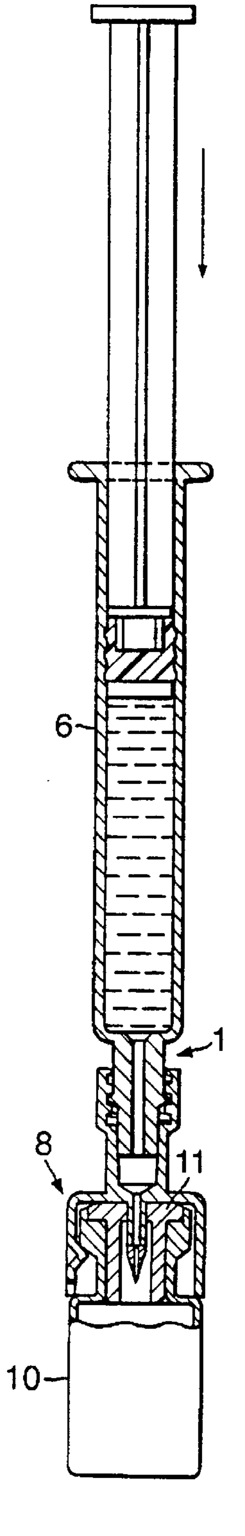
Figure 3A:
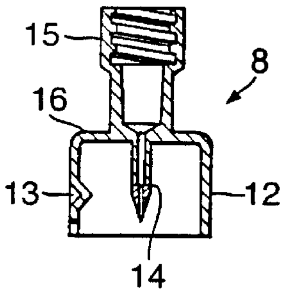

In FIG. 3, the connection means 8 shown by itself in FIG. 3A comprises a substantially bell-shaped structure 12 of internal size, shape and dimensions enabling it to fit closely over the closure (not shown in detail) including a puncturable seal, of the vial 10. The bell 12 is provided with clip means 13 to enable the bell 12 to be retained upon the vial closure. A hollow puncturing spike 14 extends downwardly internally within the bell 12 co-axially with the bell. A female internally threaded socket 15 is provided externally on the base 16 of the bell 12 and is in communication with the hollow interior of the puncturing spike 14. The internal thread of the socket 15 is engageable with the engagement parts 5 of the teat nozzle 1 such that the nozzle 1 may make a connection with the socket 15. The internal shape and dimensions of the socket 15 correspond closely to the external shape and dimensions of the nozzle 1. The puncturing spike 14 can be driven through the puncturable seal 11 of the vial 10 to thereby establish fluid communication between the contents of the vial 10 and the nozzle 1.

In use the connection means 8 may be positioned relative to a pharmaceutical vial 10 provided with a puncturable seal 11 such that the puncturing spike 14 is above and aimed at the seal 11. The means 8 is then moved downwardly toward the vial 10 such that the puncturing spike 14 punctures the seal 11 and thereby provides communication between the interior of the vial 10 and the female socket 15, 21. The nozzle 1 may then be inserted into the female socket 15 and its engagement parts 5 screwed into engagement with the internal thread of the socket 15, 21 to thereby provide communication between the syringe 6 and the interior of the vial 10, as shown in FIG. 3C.

Referring to FIG. 4 another suitable construction of the connection means 9 is shown. This comprises a skirt portion 17 of internal size, shape and dimensions enabling it to fit closely over the closure (not shown in detail) including a puncturable seal 11 of pharmaceutical vial 10, the skirt being provided with clip means 13 (of known type) to enable the skirt 17 to be retained upon the vial closure. A tubular body 18 extends upwardly when the skirt 17 is in place on the closure of vial 10 and defines an internal tubular chamber 19. Within and extending above the open top of the extension 18 is a piston 20 having a connection port in the form of an internally threaded female socket 21, and a downwardly extending hollow puncturing spike 22. The piston 20 is initially mounted in the sleeve 19 by means of a link 23 which may be easily broken, for example by a downward force on the piston, suitable links being a thin plastic film. The piston 20 may be driven downwards toward the seal 11 such that the puncturing spike 22 punctures the seal 11. The piston 20 and tubular body 18 include co-operating guides 24, 25 which encourage the piston 20 to move in a downward direction toward the vial seal, and which prevent relative rotation of the tubular body 18 and piston 20. The piston 20 and tubular body 18 also include co-operating locking means 24, 26 such that the piston 20 may be locked in place in the sleeve 19 at the lowest end of its downward movement. The locking means 24, 26 comprises a wedge-shaped projection 24 on piston 20 which snaps into and locks in a corresponding wedge-shaped hole 26 on the inner surface of body 18. The socket 21 is initially provided closed by a foil seal 27 which may be pulled off.

Figure 4A:
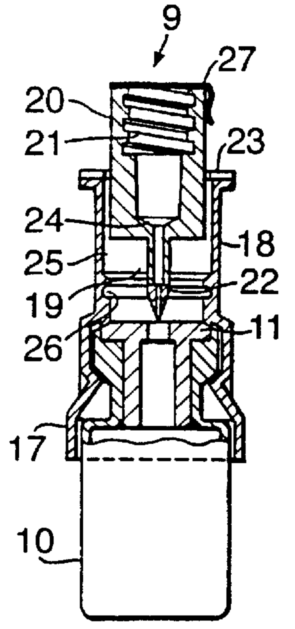
FIG. 4 shows a longitudinal sectional view through another connection means suitable for use with the device of FIGS. 1 and 2, in use.
Figure 4B:
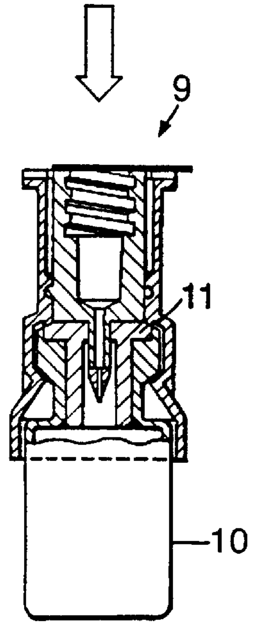
Figure 4C:
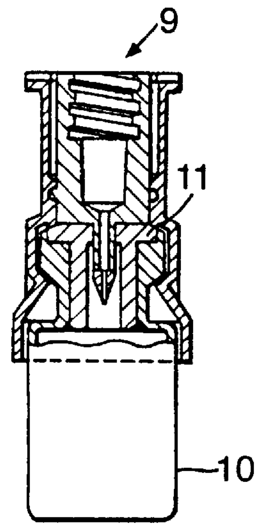
Figure 4D:
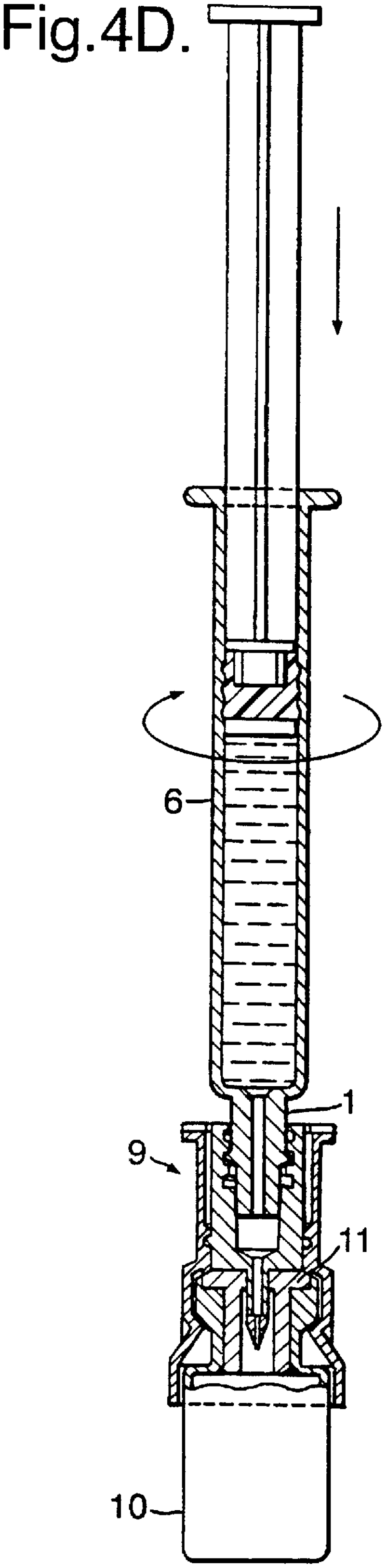

In use the connection means 9 is normally provided in place on a sealed pharmaceutical vial 10 as shown in FIG. 4A, such that the puncturing spike 22 is above and aimed at the seal 11. Force may then be applied to piston 20 to move the puncturing spike 22 downwardly, as shown in FIG. 4B, toward the vial 10 such that the puncturing spike 22 punctures the seal 11 and thereby provides communication between the interior of the vial 10 and the female socket 21. As shown in FIG. 4C the foil seal 27 is then pulled off to open the socket 21. The nozzle 1 may then be inserted into the female socket 21 and its engagement parts 5 screwed into engagement with the internal thread of the socket 21 to thereby provide communication between the syringe 6 and the interior of the vial 10, as shown in FIG. 4D. Alternatively the foil cover 27 may be peeled off first, then the nozzle of syringe 6 engaged with socket 21, and the piston 20 forced downwardly by force applied to the syringe.

Figures 5A, 5B, 5C, 5D:
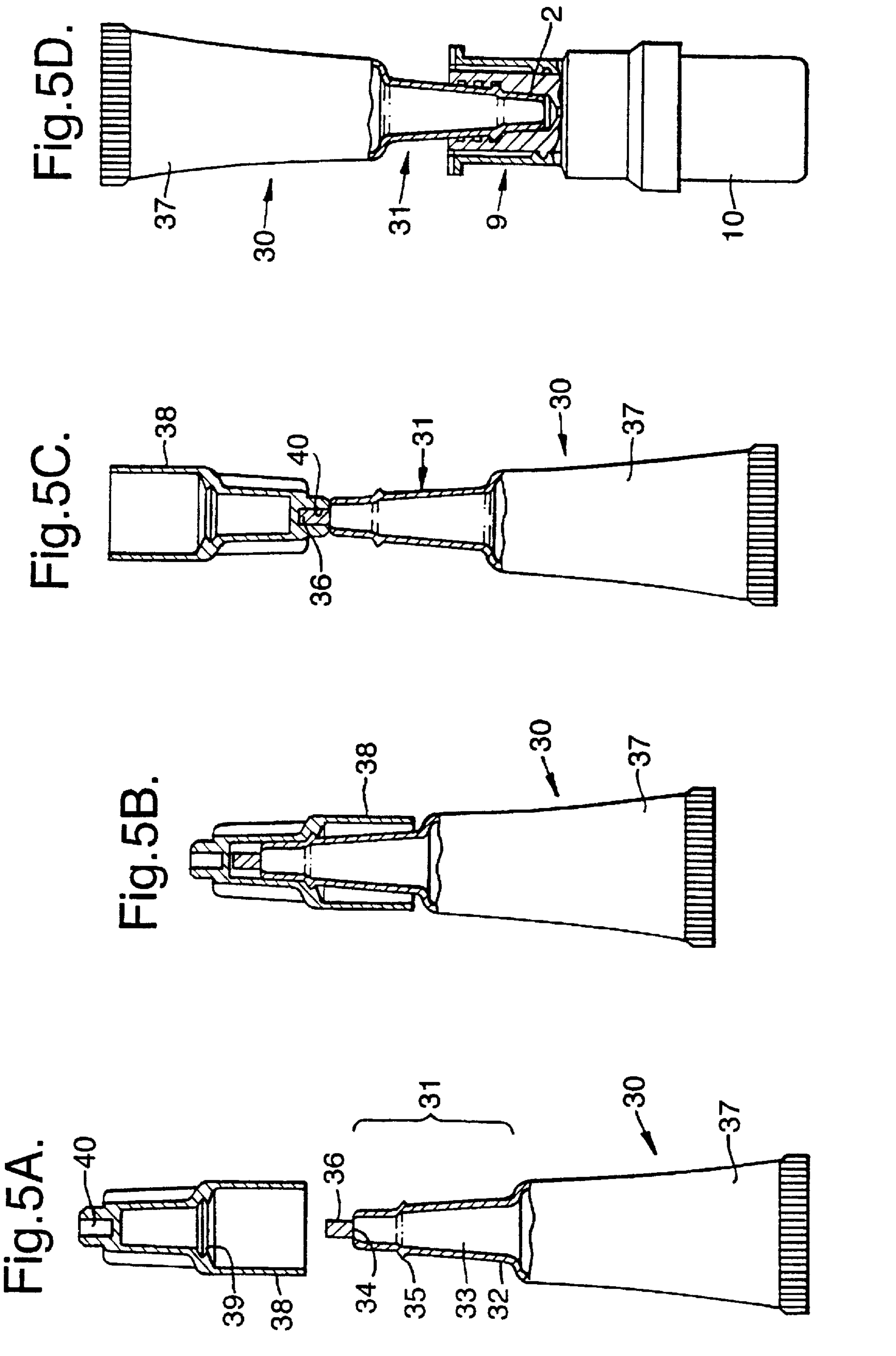
FIG. 5 shows a longitudinal sectional view through a device of the invention formed integrally as part of a dosing device being a collapsible capsule.

Referring to FIG. 5, FIG. 5A shows a dosing device suitable for paediatric oral dosing of a fluid medicament 30 (overall), of which a teat nozzle 31 forms an integral part. The teat nozzle 31 comprises a tubular conduit 32 of overall generally shallow (taper angle ca 5° ) conical shape, having an internal channel 33 along which a fluid medicament may be caused to flow toward a nozzle opening 34 of the conduit. The conduit 32 is provided externally with two engagement parts 35 in the form of two rounded bumps on the outer surface of the conduit disposed 180° apart around the circumference of the conduit 32. These bumps are substantially hemispherical and are provided upstream of the opening 34. The nozzle opening 34 is closed by a small closure 36 which is integrally but easily tearably removeably made with the rim of the opening 34.

The teat nozzle 31 is made as an integral nozzle of a collapsible capsule 37, the nozzle and capsule 37 being both made of a soft plastic such as polyethylene. The bumps 35 consequently are provided between the nozzle opening 34 distal from the capsule 37 and the end of the nozzle 31 distal to and adjoining capsule 37, about 30% of the distance from the distal end.

As shown in FIG. 5B, the teat nozzle 31 is initially provided with a protective cover 38 which may be fitted onto the teat nozzle 31 to protect and close the opening 34. The cover 38 may be made of soft plastic, e.g. the same plastic as the teat nozzle 31 and capsule 37 to resiliently fit over the teat nozzle 31, and the cover may be provided with internal concavities 39 to engage with the bumps 35.

In use, the dosing device 30 is provided with its cover 38 fitted as shown in FIG. 5B. The cover 38 is then removed as shown in FIG. 5A. The cover 38 is provided with a socket 40 which may be engaged with the closure 36 as shown in FIG. 5C, and twisting of the cover 38 then tears off the closure 36.

The now open-ended teat nozzle 31 may then be engaged with the female socket 15, 21 of connection means 8, 9 of the type shown in FIGS. 3 and 4 to enable communication with a vial 10. In FIG. 5D engagement with a connection means 9 (shown part-sectioned) and vial 10 as illustrated in FIG. 4 is shown, the bumps 35 engaging with the screw thread of the female socket 21 thereof. The connection means 8, 9 may then the used to bring the capsule 37 and vial 10 into communication in a manner analogous described to that described above.

In one mode of use the dosing syringe 6 or capsule 37 may contain a reconstitution liquid and the vial 10 may contain a solid, e.g. lyophilised, medicament for reconstitution. When the communication between the dosing syringe 6 or capsule 37 and the interior of the vial 10 has been established as described above and shown in FIGS. 3C, 4D or 5D the reconstitution liquid may be transferred through the nozzle 1, 31 socket 15, 21 and spike 14, 22 into the vial 10, and the medicament reconstituted in the vial 10. The reconstituted medicament, e.g. as a solution, may then be withdrawn into the dosing syringe 6 or capsule 37. The dosing syringe 6 or capsule 37 may then be disconnected from the connection means 8, 9, and the nozzle 1, 31 inserted gently into the mouth of a paediatric patient. By gentle operation of the syringe 6 or squeezing of the capsule 37 the made up liquid medicament may be introduced into the patient's mouth. The profile of the nozzle 1, 31 is found to be comfortable and acceptable to a paediatric patient.

What is claimed is:

1. A teat nozzle suitable for paediatric oral dosing of a fluid medicament comprising a tubular conduit having an internal channel along which a fluid medicament may be caused to flow toward a nozzle opening of the conduit, the conduit being engageable in a male-female co-operation with a female socket, wherein the conduit is provided externally with at least one engagement part which can engage with an internal helical screw thread in such a female socket, to thereby facilitate connection between the conduit and the socket, and wherein said engagement part comprises two substantially hemispherical or rounded conical bumps regularly circumferentially disposed 180° apart around the circumference of the outer surface of the conduit.

2. A teat nozzle according to claim 1, wherein the conduit is externally in the form of a substantially cylindrical tube having at least its part immediately adjacent to and upstream of the nozzle opening tapering in a shallow cone being narrowest at the nozzle opening end of the cone.

3. A teat nozzle according to claim 2, wherein the conduit comprises a conical part and an upstream cylindrical part, and the one or more engagement part(s) is/are provided upstream of the conical part or at the junction between the conical part and the cylindrical part.

4. A teat nozzle according to claim 1, wherein all or substantially all of the conduit is externally of a shallow conical shape.

5. A teat nozzle according to claim 1, wherein the conduit has a cylindrical part immediately adjacent to and extending upstream of the nozzle opening, and of a shallow conical shape over its further upstream part, the cylindrical part meeting the apex of the cone.

6. A dosing device for a liquid medicament provided with a teat nozzle as claimed in any one of claims 1 to 5.

7. A dosing device according to claim 6 wherein the teat nozzle is made integrally with the dosing device which includes a reservoir for a liquid medicament.

8. A dosing device according to claim 7 wherein the teat nozzle comprises the integral nozzle part of a dosing syringe or collapsible capsule.

9. A dosing device according to claim 6 wherein the teat nozzle is made as a separate part attachable to a dosing device and is provided at its upstream end with a suitable connection for a dosing device.

10. A kit comprising at least one dosing device as claimed in claim 6 provided in combination with a vial containing a medicament and a connection means by which the teat nozzle may be connected to the vial, the connection means comprising a female socket provided with an internal helical screw thread to engage the at least one engagement part of the conduit in a screw thread engagement.

11. A kit according to claim 10 wherein the vial has a puncturable seal, and the connection means comprises a female socket having an internal screw thread which is engageable with the engagement parts of the teat nozzle such that the nozzle may make a fluid connection with the socket, a hollow puncturing spike having an internal channel therein which is in communication with the socket, the puncturing spike able to be driven through the puncturable seal of the container to thereby establish communication between the contents of the container and the teat nozzle.

12. A kit according to claim 11 wherein the connection means comprises a substantially bell-shaped structure having an interior of internal size, shape and dimensions enabling it to fit closely over the closure, including the puncturable seal, of the vial, the structure having a base with an upper exterior surface and a lower interior surface, the hollow puncturing spike extending downwardly from the internal surface of the base internally within the bell, a female internally screw threaded socket being externally on the base of the structure and in communication with the hollow channel of the puncturing spike.

13. A kit according to claim 11 wherein the connection means comprises a tubular body which can be attached to the vial and which when in place on the vial extends upwardly from the mouth of the vial to define internally a tubular chamber having the puncturable seal at a lower end, a piston, provided in an first upper position relatively more distanced from the seal and being moveable within the tubular body to a second lower position relatively less distanced from the seal, the piston having a connection port comprising the female socket, and a tubular puncture member extending downwardly from the piston, the puncture member having a cannula therethrough communicating with the connection port, movement of the piston from its first position to its second position causing the puncture member to puncture the seal so that in the second position the connection port and the interior of the vial are in communication with each other via the cannula.

* * * * *